United States Patent
Gottfried

(10) Patent No.: US 6,551,103 B2
(45) Date of Patent: Apr. 22, 2003

(54) DENTIST ADVISORY SYSTEM

(76) Inventor: Philip H. Gottfried, 24 York Dr., New City, NY (US) 10956

( * ) Notice: Subject to any disclaimer, the term of this patent is extended or adjusted under 35 U.S.C. 154(b) by 0 days.

(21) Appl. No.: 09/931,512

(22) Filed: Aug. 16, 2001

(65) Prior Publication Data

US 2003/0036038 A1 Feb. 20, 2003

(51) Int. Cl.[7] ................................................. A61C 1/00
(52) U.S. Cl. ..................................................... 433/229
(58) Field of Search ................... 433/229, 27; 340/321, 340/825.19, 573.1; 116/173, 306, DIG. 44

(56) References Cited

U.S. PATENT DOCUMENTS

| | | | | |
|---|---|---|---|---|
| 4,455,963 A | * | 6/1984 | Matsuo | 116/200 |
| 4,810,996 A | * | 3/1989 | Glen et al. | 340/321 |
| 6,079,350 A | * | 6/2000 | Parker | 116/173 |

FOREIGN PATENT DOCUMENTS

| | | | | |
|---|---|---|---|---|
| FR | 2450602 | * | 11/1980 | 433/229 |
| WO | WO 86/03870 | * | 7/1986 | |

* cited by examiner

*Primary Examiner*—Cary E. O'Connor
(74) *Attorney, Agent, or Firm*—Amster, Rothstein & Ebenstein

(57) ABSTRACT

A dentist advisor system includes signaling apparatus by which a patient can non-verbally advise a dentist to interrupt or terminate a dental procedure being performed by the dentist positioned on one side of the patient, and a selected tactile surface selectively operatively associating the signaling apparatus with the hand of the patient on the side of the patient opposite the dentist. Thus the patient's associated selected hand is opposite the dentist during performance of the procedure, and thus use thereof does not interfere with the dentist.

12 Claims, 1 Drawing Sheet

DENTIST ADVISORY SYSTEM

BACKGROUND OF THE INVENTION

The present invention relates to a dentist advisory system, and more particularly to a system enabling a patient to safely and effectively advise the dentist to interrupt or terminate a dental procedure.

Since frequently a dental patient cannot verbally advise the dentist to interrupt or terminate a dental procedure being performed by the dentist because the patient's mouth contains a variety of dental instruments, it is necessary for the patient to be able to safely and effectively non-verbally advise the dentist. The dentist is typically positioned on one side of the patient, and it is the natural inclination of the patient to use the hand on that side to signal the dentist precisely because it is more proximate the dentist. This natural inclination is not only wrong, but may be ineffective and/or dangerous.

Typically the patient's hand adjacent to the dentist is not the hand of the patient most visible to the dentist's line of vision at the time the dentist is performing a procedure and thus is less likely to be seen by the dentist. In any case, the patient raising his hand on the side adjacent to the dentist may interfere with one or more of the various dental instruments and devices which are partially within and partially without the patient's mouth, and may even unintentionally jar the working hand of the dentist such that the dentist accidentally injures the patient.

While the unmedicated adult patient will normally be able to follow the prior instructions of the dentist as to the appropriate hand for advising the dentist to interrupt or terminate a dental procedure (that is, the hand on the side of the patient opposite or remote from the dentist), small children and mentally impaired adult patients may not be able to control the natural impulse, regardless of the instructions provided by the dentist. Even in the case of the normal adult patient, depending upon the type of medication used to anaesthetize the patient, the medicated patient may pursue his normal impulse and forget the instructions of the dentist. For example, under the influence of nitrous oxide (commonly known as "laughing gas"), a patient may well temporarily forget the dentist's instructions and attempt to advise the dentist with the wrong hand (that is, the hand proximate the dentist).

Additionally, even though a patient may be informed by the dentist that the dental procedure will be interrupted or terminated if the patient advises the dentist to do so, it may be helpful for the patient to have means to continuously reassure himself that he has some control over the dental procedure being performed (that is, that he can advise the dentist to interrupt or terminate the same). To this end it is desirable for the patient to have a tactile reminder or symbol of his control over the situation in order to provide continuous reassurance to the patient.

Accordingly, it is an object of the present invention to provide a dentist advisory system which enables the patient to safely and effectively advise the dentist to interrupt or terminate a dental procedure being performed by the dentist.

Another object is to provide such a system which continuously reminds the patient as to which hand should be used to provide such advice.

A further object is to provide such a system with means for focusing the attention of the patient on the appropriate hand for rendering such advice to the dentist.

It is also an object of the present invention to provide such a system having means for reassuring the patient that the patient can safely advise the dentist to interrupt or terminate the procedure by means of the patient's appropriate hand.

SUMMARY OF THE INVENTION

It has now been found that the above and related objects of the present invention are obtained in a dentist advisory system comprising means for a patient to advise a dentist to interrupt or terminate a dental procedure being performed by the dentist positioned on one side of the patient, and means to selectively operatively associate the advising means with a hand of the patient on the side of the patient opposite the dentist. Thus the patient's associated selected hand is opposite the dentist during performance of the procedure and thus does not interfere therewith.

The advising means is preferably visual. The associating means is preferably releasably fastenable to the selected hand, optionally to a finger of the selected hand.

In a preferred embodiment either the associating means or the advising means defines a selected tactile surface for reassuring the patient that the patient can safely advise the dentist to interrupt or terminate the procedure by use of the patient's associated selected hand. The tactile surface is preferably foraminiferous.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with accompanying drawing wherein.

DETAILED DESCRIPTION OF THE PREFERRED EMBODIMENTS

Figure 1:
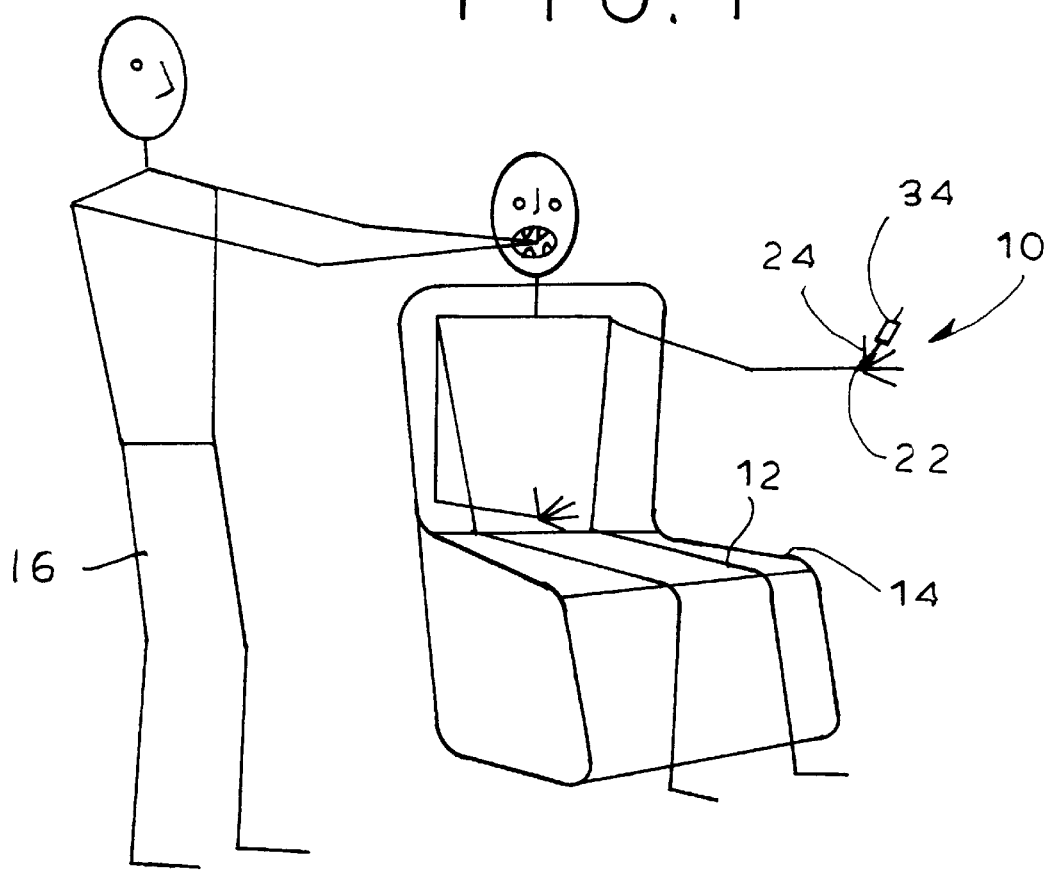
FIG. 1 is a schematic representation of a patient in a dental chair, and a dentist performing a dental procedure on the patient from one side of the patient, the patient having advising means associated with his hand on the other side.

Referring now to the drawing, and in particular to FIG. 1 thereof, the dentist advisory system according to the present invention, generally designated by the reference numeral 10, is typically used in a conventional dental office setting. Such a setting is schematically illustrated in FIG. 1 which shows a patient 12 seated in a dental chair 14 with a dentist 16 positioned on and adjacent a first side of the patient.

Figure 2:
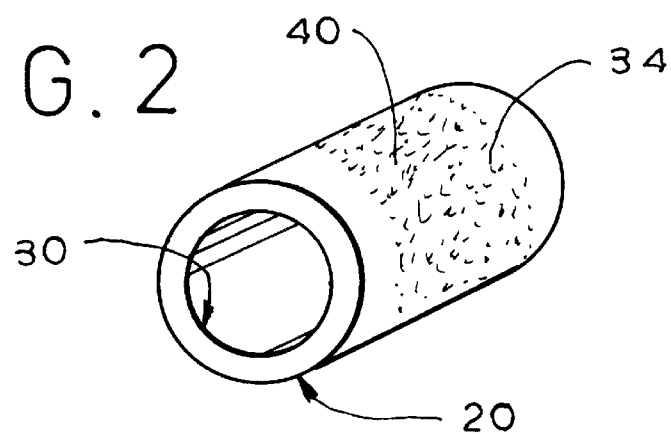
FIG. 2 is an isometric view of a signaling ring worn by the patient on a finger of his hand opposite the dentist.

Referring now also to FIG. 2, according to the present invention the dentist 16 has provided the patient 12 with means, generally designated 20, for advising the dentist 16 to interrupt or terminate a dental procedure being performed by the dentist 16. The advising means 20 is preferably visual in nature. Prior to commencing the dental procedure, the dentist 16 selectively operatively associates the advising means 20 with the hand 22 of the patient 12 on a second side of the patient 12—namely, the side opposite and remote from the dentist. Thereafter the patient 12 may deploy the advising means 20 associated with the associated selected hand 22 during performance of the procedure and not accidentally interfere therewith. The associating means, generally designated 30, is preferably releasably fastenable to the selected hand 22 or a portion thereof. For example, where the associating means 30 is a glove, the glove may be releasably fastened to (that is, worn on) the selected hand 22. Where the associating means 30 is a ring 34, as is illustrated, the ring may be releasably fastened to (that is, worn on) a finger 24 of the selected hand 22. In either case, the patient 12 may effectively and safely advise the dentist 16 to interrupt or terminate the dental procedure being performed by the dentist 16 simply by raising the selected hand 22 associated with the advising means 20.

It will be understood that each of the advising means 20 and the associating means 30 may be parts of a single larger entity. For example, in the case of a glove, the outer surface of the glove may be or contain the advising means 20, while the inner surface of the glove is the associating means 30. The glove outer surface is readily visible to the dentist 16, while the inner surface of the glove, when worn, is typically not visible to the dentist 16. Nonetheless, the inner surface of the glove performs its function of associating the outer surface with the selected hand 22. Similarly, in the case of a ring 34, the outer surface may be or contain the advising means 20, while the inner surface is the associating means 30 which associates the outer surface with the selected finger 24. The integration of the advising and associating means 20, 30 into a single structure is preferred as it reduces the chance of one of the two means 20, 30 becoming lost. The advising means 20 need not be a whole surface of the structure; for example, if preferred, only the outer surface of the palm of the glove may serve as the advising means 20.

Preferably the advising means 20, the associating means 30 or both define a selected tactile surface 40 for reassuring the patient 12 that he can safely advise the dentist 16 to interrupt or terminate the procedure by use of the patient's associated selected hand 22—that is, the hand associated with the advising means 20 by the associating means 30. While a wide variety of tactile surfaces may be used for this purpose, a preferred surface 40 is foraminiferous. The sensing of the tactile surface 40 by the patient's associated selected hand 22 will reassure the patient that he has control of the procedure—that is, he can effectively and safely advise the dentist to interrupt or terminate the procedure, simply by use of the appropriate hand 22. It is theorized that the conceptual association of the tactile surface 40 and the associated selected hand 22 will remain intact, notwithstanding youth, age or medication level, since the tactile surface 40 provides a self-reinforcing psychological reassurance that a dental patient typically desires. In other words, the patient's attention will be concentrated on the associated selected hand 22 rather than the hand adjacent to the dentist. For example, if the pain associated with a particular moment in a dental procedure temporarily overcomes the dream world typically provided by laughing gas medication, the patient will instantaneously associate the tactile surface 40 with the appropriate hand 22 for use in advising the dentist.

To summarize, the present invention provides a dentist advisory system which enables the patient to safely and effectively advise the dentist to interrupt or terminate a dental procedure being performed by the dentist. The system continuously reminds the patient as to which hand should be used to provide such advice, and includes means for focusing the attention of the patient on the appropriate hand for rendering such advice to the dentist. Further, the system has means for reassuring the patient that the patient can safely advise the dentist to interrupt or terminate the procedure by means of the patient's appropriate hand.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

I claim:

1. A non-electrical dentist advisory system comprising:
   (A) means of an exclusively mechanical nature for a patient to visually advise a dentist to interrupt or terminate a dental procedure being performed by the dentist positioned on one side of the patient; and
   (B) means to selectively operatively associate said advising means with a hand of the patient on the side of the patient opposite the dentist, without reliance on the volition of the patient, whereby the patient's associated selected hand is opposite the dentist during performance of the procedure and thus does not interfere therewith.

2. The system of claim 1 wherein said associating means removably affixes said advising means to the patient's associated selected hand.

3. A non-electrical dentist advisory system comprising:
   (A) means of an exclusively mechanical nature for a patient to visually advise a dentist to interrupt or terminate a dental procedure being performed by the dentist positioned on one side of the patient; and
   (B) means to selectively operatively associate said advising means with a hand of the patient on the side of the patient opposite the dentist, whereby the patient's associated selected hand is opposite the dentist during performance of the procedure and thus does not interfere therewith;
   one of said advising means and said associating means defining a selected tactile surface for reassuring the patient that the patient can safely advise the dentist to interrupt or terminate the procedure by use of the patient's associated selected hand.

4. A dentist advisory system comprising:
   (A) means for a patient to advise a dentist to interrupt or terminate a dental procedure being performed by the dentist positioned on one side of the patient; and
   (B) means to selectively operatively associate said advising means with a hand of the patient on the side of the patient opposite the dentist during performance of the procedure and thus not interfere therewith;
   one of said advising means and said associating means defining a selected tactile surface for reassuring the patient that the patient can safely advise the dentist to interrupt or terminate the procedure by use of the patient's associated selected hand, said tactile surface being foraminiferous.

5. A non-electrical dentist advisory system comprising:
   (A) means of an exclusively mechanical nature for a patient to visually advise a dentist to interrupt or terminate a dental procedure being performed by the dentist positioned on one side of the patient; and
   (B) means to selectively operatively associate said advising means with a hand of the patient on the side of the patient opposite the dentist, whereby the patient's associated selected hand is opposite the dentist during performance of the procedure and thus does not interfere therewith;
   said associating means being releasably fastenable to the selected hand.

6. A dentist advisory system comprising:
   (A) means for a patient to advise a dentist to interrupt or terminate a dental procedure being performed by the dentist positioned on one side of the patient; and (B) means to selectively operatively associate said advising means with a hand of the patient on the side of the patient opposite the dentist, whereby the patient's associated selected hand is opposite the dentist during performance of the procedure and thus does not interfere therewith; said associating means being releasably fastenable to a finger of the selected hand.

7. The system of claim 6 wherein said associating means is in the nature of a ring to be worn on the finger.

8. A non-electrical dentist advisory system comprising means to selectively operatively associate, without reliance on the volition of the patient:

(A) a visual signal to advise a dentist to interrupt or terminate a dental procedure being performed by the dentist positioned on one side of the patient; and (B) a hand of the patient on the side of the patient opposite the dentist;

whereby the patient's associated selected hand is opposite the dentist during performance fo the procedure and thus does not interfere therewith.

9. A non-electrical dentist advisory system comprising means to selectively operatively associate:

(A) a visual signal to advise a dentist to interrupt or terminate a dental procedure being performed by the dentist positioned on one side of the patient; and (B) a hand of the patient on the side of the patient opposite the dentist;

whereby the patient's associated selected hand is opposite the dentist during performance of the procedure and thus does not interfere therewith;

said associating means defining a selected tactile surface for reassuring the patient that the patient can safely advise the dentist to interrupt or terminate the procedure by use of the patient's associated selected hand.

10. The system of claim 9 wherein said selected tactile surface is foraminiferous.

11. A non-electrical dentist advisory system comprising means to selectively operatively associate:

(A) a visual signal to advise a dentist to interrupt or terminate a dental procedure being performed by the dentist positioned on one side of the patient; and (B) a hand of the patient on the side of the patient opposite the dentist;

whereby the patient's associated selected hand is opposite the dentist during performance of the procedure and thus does not interfere therewith;

said associating means being releasably fastenable to a finger of the selected hand.

12. The system of claim 11 wherein said associating means is in the nature of a ring to be worn on the finger.

* * * * *